(12) United States Patent
Kensicher et al.

(10) Patent No.: US 8,637,579 B2
(45) Date of Patent: Jan. 28, 2014

(54) PROCESS TO THICKEN AQUEOUS COMPOSITIONS BY MEANS OF ORGANOPHOSPHATE POLYMERS

(75) Inventors: Yves Kensicher, Theize (FR); Jean-Marc Suau, Lucenay (FR)

(73) Assignee: Coatex S.A.S., Genay (FR)

( * ) Notice: Subject to any disclaimer, the term of this patent is extended or adjusted under 35 U.S.C. 154(b) by 812 days.

(21) Appl. No.: 12/227,312

(22) PCT Filed: Jun. 1, 2007

(86) PCT No.: PCT/IB2007/001515
§ 371 (c)(1),
(2), (4) Date: Jul. 28, 2010

(87) PCT Pub. No.: WO2007/144721
PCT Pub. Date: Dec. 21, 2007

(65) Prior Publication Data
US 2010/0292347 A1    Nov. 18, 2010

(30) Foreign Application Priority Data
Jun. 9, 2006   (FR) ..................................... 06 05103

(51) Int. Cl.
*A61K 47/32* (2006.01)
*C08K 3/00* (2006.01)
*C11D 17/08* (2006.01)
*C08L 43/02* (2006.01)

(52) U.S. Cl.
USPC ............. 514/772.4; 524/3; 524/547; 510/436

(58) Field of Classification Search
None
See application file for complete search history.

(56) References Cited

U.S. PATENT DOCUMENTS

| 4,277,593 | A * | 7/1981 | Scheve ........................... 526/279 |
| 4,782,120 | A * | 11/1988 | Rousset et al. ............. 525/326.6 |
| 7,902,310 | B2 * | 3/2011 | Einfeldt et al. ................ 526/221 |
| 2001/0049419 | A1* | 12/2001 | Mallo et al. ................ 525/328.5 |
| 2005/0245406 | A1* | 11/2005 | Scherer et al. ................ 508/469 |
| 2007/0122443 | A1* | 5/2007 | Narayanan et al. ........... 424/423 |

FOREIGN PATENT DOCUMENTS

| DE | 102005022843 | * 11/2006 | ................ C07F 9/06 |
| EP | 1 617 277 A | 1/2006 | |
| EP | 1617277 | * 1/2006 | |
| FR | 2 536 758 A1 | 6/1984 | |
| FR | 2 637 511 A1 | 4/1990 | |

OTHER PUBLICATIONS

The International Search Report for PCT Application No. PCT/IB2007/001515.
The Written Opinion for PCT Application No. PCT/IB2007/001515.

* cited by examiner

*Primary Examiner* — Anoop Singh
*Assistant Examiner* — Anna Falkowitz
(74) *Attorney, Agent, or Firm* — Amster, Rothstein & Ebenstein LLP

(57) ABSTRACT

A first object of the invention is a process for thickening of an aqueous composition, through the introduction into the said composition for thickening of at least one polymer, characterized in that the said polymer contains at least one anionic monomer, which is an organophosphate monomer.

21 Claims, 3 Drawing Sheets

PROCESS TO THICKEN AQUEOUS COMPOSITIONS BY MEANS OF ORGANOPHOSPHATE POLYMERS

Figure 1:
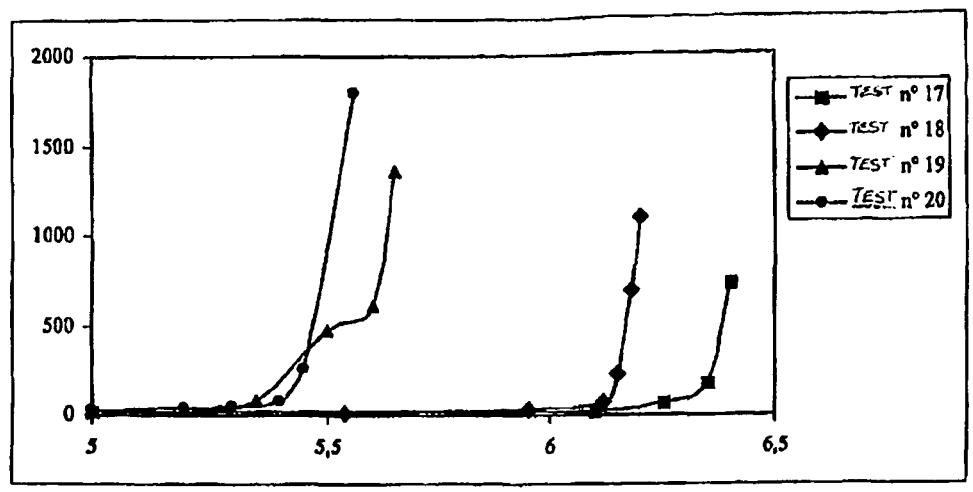

This is a U.S. national phase of PCT Application No. PCT/EP2007/001515, filed Jun. 1, 2007, and claims priority to French Application No. 06/05103, filed Jun. 9, 2006.

A first object of the invention is a process for thickening of an aqueous composition, through the introduction into the said composition for thickening of at least one polymer, characterised in that the said polymer contains at least one anionic monomer, which is an organophosphate monomer.

A second object of the invention consists of the aqueous compositions thus thickened, and containing the said polymers.

In the field of aqueous formulations used in cosmetics, such as shampoos, soaps or creams, there is a requirement for the skilled man in the art—who is the formulator of such compositions—to thicken such products, in a pH range matching that of skin, i.e. pH values of between 5 and 7, and preferentially of between 5 and 6.5, and very preferentially of between 5.5 and 6.

In order to resolve this problem the skilled man in the art is familiar with a number of documents which can be divided into 3 categories, according to the technical solutions they propose: use of polymers in the form of powders, the technique known as "back-acid", and finally the use of polymers in the form of emulsions.

In the first category the skilled man in the art is familiar with document EP 1 138 703 A1, which describes a cosmetic, dermo-cosmetic pharmaceutical or dermo-pharmaceutical topical composition containing 0.1% to 10% by weight of a polymer, whether linear, branched or cross-linked, with a basis of at least one monomer having a free strong acid group such as a sulphonic or phosphonic group, which is partially or totally salified, copolymerised with a least one monomer chosen from among the aliphatic alcohol esters with 8 to 30 carbon atoms and unsaturated monocarboxylic acids, or from among the aliphatic alcohol esters with 8 to 30 carbon atoms and unsaturated polycarboxylic acids. The abovementioned polymer is an emulsifying polymer, in solid form, which can be dispersed in water [0003]; it enables the composition which contains it to be thickened, notably for pH values greater than or equal to 5 [0025]. However, there is no example which demonstrates this latter property. In addition, the mechanism for thickening of these polymers is not explained in detail in this document and, even more importantly, there is no information on the claimed thickening mechanism of these polymers at pHs of lower than 7.

The skilled man in the art is also familiar with the technique known as "back-acid", as described, for example, in document WO 01/76 552, which describes a process enabling thickening in an aqueous medium, where the said process consists in introducing into the said aqueous medium a surfactant and a rheology modifier, which is a cross-linked and alkali-soluble acrylic copolymer, and then in increasing the pH to a value of greater than 5 (preferentially 6 and very preferentially 6.5), through the use of an alkaline product, and then in reducing the pH (between 3 and 6, notably for cosmetic applications) to the desired value through the addition of an acid compound (method described from page 27 line 25 to page 28 line 21). Such an acrylic copolymer does, indeed, produce a thickening effect in an aqueous medium when its carboxylic acid groups are neutralised, which causes an ionic repulsion mechanism leading to an increase in the viscosity of the medium (page 1, lines 2 to 8); this mechanism is distinguished notably from the thickening mechanism, which is also mentioned in this document (page 1, lines 8 to 10) and with which the skilled man in the art is very familiar. It consists in the use of polymers consisting of a long hydrophilic backbone, on to which are grafted chains with a hydrophobic grouping which, when introduced into water, will lead to associations between the hydrophobic groupings: a three-dimensional network is then created which leads to an increase of the viscosity of the medium.

Lastly, the skilled man in the art is familiar with a number of documents which describe the use of polymers in emulsion.

He is familiar, notably, with document EP 1 493 774 A2, which describes an aqueous composition for a topical application, containing a physiologically acceptable medium and at least one water-soluble polymer, constituted by a water-soluble backbone with a basis of 2-acrylamido-2-methylpropane sulphonic acid, and by lateral chains comprising at least one polyoxyethylene unit and a least one polyoxypropylene or polyoxybutylene unit. These polymers in emulsion enable a thermogelifying effect to be obtained in a narrow temperature range, which enables a clearer fluid/gel transition to be obtained on application on to skin of the cosmetic composition containing them. It is also indicated that such polymers in emulsion are insensitive to the pH, although no example illustrates any thickening effect for pH values of less than 7. All these properties are attributed by the inventors [0011 and 0012] to the presence of the abovementioned units and grafted on to the backbone, unlike polymers with a statistical distribution of the different monomeric units.

The skilled man in the art is also familiar with document EP 0 824 914 B1, which resolves the problem of thickening of cosmetic formulations, both with acid and basic pHs. The solution which he proposes consists in the use of a polymer in emulsion comprising at least one associative monomer, at least one alkyl ester monomer of acrylic or methacrylic acid, and a least one monomer chosen from the group consisting of the heterocyclic compounds with a vinyl substituent having at least one nitrogen or sulphur atom, methacrylamide, a methacrylate of mono- or di-(alkyl at C1 to C4)amino(alkyl at C1 to C4), a mono- or di-(alkyl at C1 to C4)amino(alkyl at C1 to C4) methacrylamide. On reading this document, it appears however that it is the mandatory presence of an aminated cationic monomer which enables aqueous media with acid pHs to be thickened: all the examples, indeed, use dimethylaminoethyl methacrylate as the monomer used in the composition of the polymers according to this invention. This document uses a thickening mechanism at a pH lower than 7 which is well-known to the skilled man in the art: it is the presence of an aminated cationic monomer, which will be ionised at an acid pH, and cause the thickening mechanism by this means.

Another example of a thickening mechanism at pH values of less than 7 is described in document WO 2004/024 779, which also seeks to resolve the problem of thickening at acid pHs. The solution it describes consists in the use in an emulsion of associative polymers of a cationic nature, where the cationic character is contributed by a substituted amino vinylic monomer. In this case it is, simultaneously, the presence of a cationic monomer and the associative thickening mechanisms as previously described which come into play.

The skilled man in the art is also familiar with document U.S. Pat. No. 4,529,773 B1, which consists in thickening an aqueous medium by the stages of introduction of a alkali-soluble but not water-soluble thickening emulsion, and of a surfactant, of neutralising the medium to a pH of higher than 6.5, and finally of acidifying the medium by bringing the pH down once again to a value of less than 6.5. The key is therefore the combination of the previously described back-acid mechanism, and the use of a polymer in the form of an emulsion in the presence of a surfactant. In this document the inventors describe the origin of the low-pH thickening mechanism as follows: the thickening effect of the polymer is "activated" (column 3, lines 41-52) when it is neutralised to a pH close to 7, and this activation is maintained even when the pH is reduced again through the presence of the surfactant.

Finally, and still in the field of polymers in emulsion, the skilled man in the art is familiar with a number of documents which describe the use of polymers in emulsion as thickening agents, where the said polymers notably contain a phosphonic group.

The skilled man in the art is familiar with document EP 1 371 692, which describes emulsions with a auto reversible microlatexbasis containing at least one polymer having in a particular variant a strong acid group which is the sulphonic or phosphonic acid group.

He is also familiar with document FR 2 810 545, which describes reverse emulsions containing at least one polymer, having at least one weak acid group and at least one strong acid group, where the said strong acid group according to a particular variant of this invention is the sulphonic or phosphonic acid group.

He is also familiar with document FR 2 856 691, which describes a thickening emulsion containing water, an emulsifying agent and a polyelectrolyte which can have a strong acid group, where the said strong acid group can be the sulphonic or phosphonic acid group. However, none of the abovementioned documents seeks to resolve the problem of thickening at pHs of lower than 7.

Finally, the skilled man in the art is familiar with document WO 03/62 288, which concerns the technical problem of the development of polymers in emulsion, notably for cosmetic applications, having particular rheological profiles, such as the possibility of manufacturing gels with low shearing rates, where the gel character is retained when the shearing rate increases. According to a particular advantage of this invention, the said polymers enable aqueous formulations to be thickened in a broad pH range, since at a rate of 1% by dry weight in water the said polymers lead to a Brookfield™ viscosity (at 20 revolutions/minute) of less than 1,000 mPa·s and 100,000 mPa·s for a pH of between 3 and 9, and to a Brookfield™ viscosity (at 20 revolutions/minute) of less than 1,000 mPa·s for a pH of between 5.5 and 8.5. To resolve these technical problems, document WO 03/62 288 describes a solution which lies in an associative and alkali-soluble polymer, manufactured as an emulsion, consisting:
  a) of at least one vinylic acid monomer chosen from among the carboxylic vinylic monomers, or sulphonic vinylic or phosphonic vinylic monomers,
  b) of at least one non-ionic vinylic monomer,
  c) of at least 2 associative monomers terminated by a hydrophobic group, where the hydrophobic groups, when chosen from the same hydrocarbon class for both monomers, must then differ by at least 8 carbon atoms,
  d) possibly of at least one other monomer chosen from among a cross-linking monomer, a transfer agent or their blends.

As acknowledged by the authors of this document, who themselves designate the abovementioned polymer in emulsion by the term "alkali-soluble associative polymer", the thickening mechanism is, here, both of the associative type and of the alkali-soluble type (i.e. there is an activation of the thickening effect for acid pH values).

Therefore, continuing its research with a view to thickening aqueous compositions effectively, notably at pHs of lower than 7, the Applicant has developed a process for thickening an aqueous composition, through the introduction into the said composition for thickening of at least one polymer, characterised in that the said polymer contains at least one anionic monomer which is an organophosphate monomer.

In a completely surprising manner, use of such a process enables a thickening effect of an aqueous composition containing the said polymer with an organophosphate monomer to be obtained at acid pH values, and notably at pH values less than those at which the thickening effect appears for the use of the same quantity of a thickening polymer of the prior art.

In the abovementioned state of the technique, the Applicant firstly stresses that no document reveals the use of a polymer containing at least one anionic monomer which is an organophosphate monomer, with a view to thickening an aqueous composition. Still less, none of these documents reveals this use to obtain a thickening effect at pHs of lower than 7.

Without wishing to be linked to any particular theory, it is the opinion of the Applicant that the presence of an organophosphate monomer, which is easily ionised at a pH of lower than 7, enables improved solubilisation of the polymer, and therefore a notably marked thickening effect at these pH values. One of the merits of the Applicant therefore resides in the fact that it has been able to observe that the possible ionisation of certain monomers of the thickening polymer, where this ionisation occurs at more acid pH values than for polymers of the prior art, such as polycarboxylates, and leading to a satisfactory solubilisation of the polymer at these same pH values, was a mechanism which could enable the thickening effect to be activated.

This merit appears to be particularly great, on reading the abovementioned documents of the prior art, since the latter teach numerous and varied thickening mechanisms (back-acid technique, activation of a polymer in an acid medium, distribution of units of hydrophobic links in a hydrophilic chain, associative mechanism, alkali-soluble polymers, polymers which are both associative and alkali-soluble), with a view to thickening of aqueous formulations at pHs of lower than 7. Nothing would therefore in principle induce the skilled man in the art to choose one of these mechanisms rather than another.

In addition, the Applicant has been able to identify, through the choice of at least one anionic monomer, which is an organophosphate monomer, a particular family of monomers which was going to give the desired effect, i.e. that the said monomers were going to be ionised more easily than the thickening polymers of the prior art, at pH values of less than 7. Such that solubilisation of the polymer containing the said monomer is facilitated in an acid medium, and allows development of a thickening mechanism the effects of which were revealed to be completely surprising compared to thickening polymers of the prior art without such organophosphate monomers.

In addition, the Applicant emphasises that the process according to the invention enables use as thickening agents of the said polymers containing at least one organophosphate monomer, either in powder form, or in the form of an emulsion, or in the form of a solution, which constitutes another advantage of the present invention, in terms of possibilities open to the user.

Finally, the Applicant indicates that polymers containing an organophosphate monomer are already known, and notably described in document WO 01/74909. This document describes, indeed, a process for synthesis in emulsion of a polymer consisting of a polymerisable monomer and a polymerisable ester surfactant of formula $R_1$—C(O)—$R_2$—X, where $R_1$ designates a substituted vinyl radical, $R_2$ designates a divalent polyalkylene radical having at least 2 oxyalkylenic groupings, and X designates a phosphate grouping. These polymers are used for the manufacture of latex, and subsequently used in paints. There is, moreover, no teaching in this document, on the subject of a possible rheological modification which might be caused by the polymers used.

The Applicant is also familiar with document FR 2 536 758, which describes additives for fluidification of aqueous drilling muds, with the aim of retaining their rheological properties under extreme temperature and pressure conditions, characterised in that they are water-soluble copolymers resulting from the copolymerisation of ethylenic acids, acrylamides and ethylenic esters of phosphoric acid.

Finally, the Applicant is also familiar with document FR 2 637 511, which describes compatibility, dispersion and grinding agents for pigmentary aqueous suspensions formulated from minerals at least one of which is a sulphate, with a view to cancelling the viscosifying effect caused by the presence of the said sulphate, and having the characteristic (among others) that they have a phosphate or phosphonate group.

In conclusion, on the subject of these last 3 documents: not only do they not disclose or suggest the use as thickening agents of polymers containing an organophosphate group but, on the contrary, 2 of them teach that copolymers having one ethylenic ester group of phosphoric acid (FR 2 536 758) or having a phosphate or phosphonate group (FR 2 637 511) leads to polymers which tend to reduce the viscosity of the medium (fluidifying agents in the case of document FR 2 536 758 and agents cancelling the viscosifying effect in document FR 2 637 511). And the skilled man in the art wishing to resolve the technical problem posed in the present Application is seeking precisely the contrary. Consequently these 3 documents indeed encouraged the skilled man in the art not to use polymers containing at least one anionic monomer which is an organophosphate monomer, in order to thicken aqueous formulations, and still less in order to thicken such formulations at pHs lower than 7.

One of the distinctive characteristics between the polymers of the present invention and the polymers used in the 2 above-mentioned documents lies in their molecular weights. In document FR 2 637 511, the polymers have a specific viscosity of less than 10 (in the case of a homopolymer of acrylic acid, this means that the molecular weight is less than 50,000 g/mole) and in document FR 2 536 758 they have a molecular weight of less than 50,000 g/mole. The polymers of the present invention have a molecular weight of greater than 80,000 g/mole, preferentially greater than 100,000 g/mole, and very preferentially greater than 120,000 g/mole (the measuring method is indicated at the start of the examples).

A first object of the invention is therefore a process for thickening of an aqueous composition, through the introduction into the said composition for thickening of at least one polymer, characterised in that the said polymer contains at least one anionic monomer, which is an organophosphate monomer.

This process is also characterised in that the organophosphate monomer is chosen from among molecules with the following formulae:

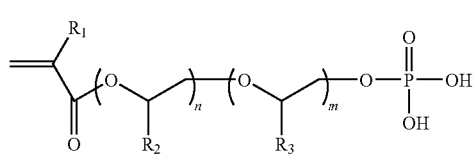

$R_1$: H, $CH_3$
$R_2$: H, $CH_3$
$R_3$: H, $CH_3$ (Ia)

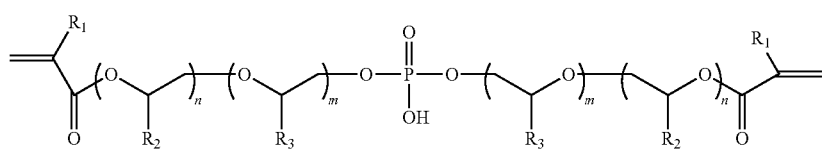

$R_1$: H, $CH_3$
$R_2$: H, $CH_3$
$R_3$: H, $CH_3$ (Ib)

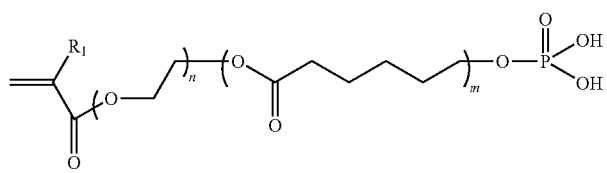

$R_1$: H, $CH_3$ (Ic)

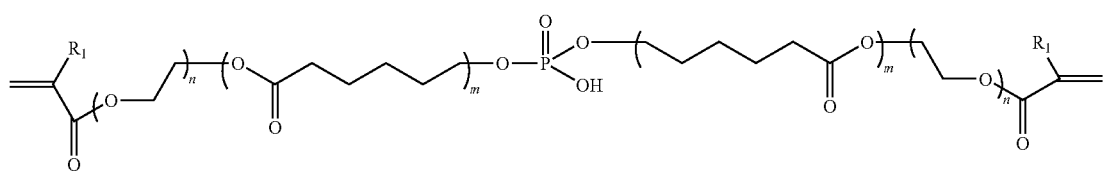

$R_1$: H, $CH_3$ (Id)

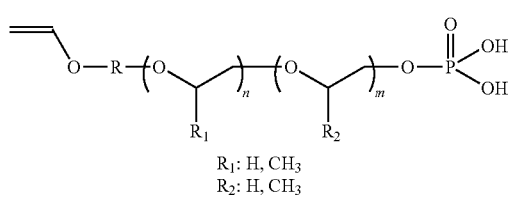

(Ie)

R₁: H, CH₃
R₂: H, CH₃

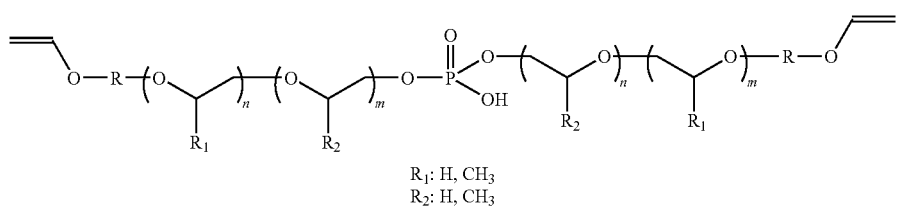

(If)

R₁: H, CH₃
R₂: H, CH₃

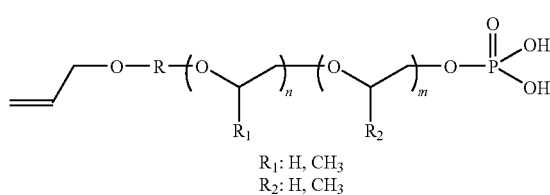

(Ig)

R₁: H, CH₃
R₂: H, CH₃

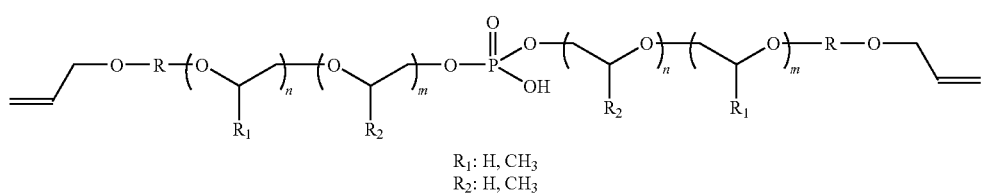

(Ih)

R₁: H, CH₃
R₂: H, CH₃ and their blends, where n designates an integer of between 1 and 100, and preferentially between 1 and 20, where m designates an integer of between 0 and 100, and preferentially of between 0 and 20, and R designates an alkyl chain having 2 to 8 carbon atoms.

This process is also characterised in that the said composition for thickening has a pH of between 5 and 7, preferentially between 5 and 6.5, and very preferentially between 5.5 and 6.

This process is also characterised in that the said polymer is introduced into the aqueous composition for thickening in powder form, and/or in the form of an aqueous dispersion, and/or in the form of a solvent-based dispersion, and/or in the form of a reverse dispersion, and/or in the form of an aqueous solution, and/or in the form of a solvent-based solution.

By an "aqueous dispersion" the Applicant means the dispersion of the said polymer in the form of stable particles, in a continuous phase consisting of water (the term "direct emulsion" will also be used).

By a "solvent-based dispersion" the Applicant means the dispersion of the said polymer in the form of stable particles, in a continuous phase consisting of at least one solvent.

By "reverse dispersion" the Applicant means a medium consisting of a phase containing the said polymer and water, where the said phase is dispersed in a continuous organic phase (the term "reverse emulsion" will also be used).

By "aqueous solution" the Applicant means a medium consisting of the said polymer dissolved in an aqueous phase.

By a "solvent-based solution" the Applicant means a medium consisting of the said polymer dissolved in a solvent-based phase.

This process is also characterised in that it can also use the back-acid technique, i.e. that it includes the stages of introduction of the said polymer into the aqueous composition for thickening, of introduction of an alkaline compound enabling the pH value to be increased to a value greater than 5, preferentially greater than 6, and very preferentially greater than 6.5, and of reduction of the pH value by means of an acid compound to a value of less than 7, preferentially less than 6.5, and very preferentially less than 5.5.

This process is also characterised in that the said polymer may also contain:
a) at least one other anionic monomer different to the organophosphate monomer,
b) and/or at least one vinylic non-ionic monomer,
c) and/or at least one non-ionic monomer with a hydrophobic grouping,
d) and/or at least one organofluorate or organosililate monomer or their blends,
e) and/or at least one cross-linking monomer, i.e. a monomer having at least 2 polymerisable links, where the said monomer is different from the organophosphate monomers of formulae (Ib), (Id), (If), and (Ih).

This process is also characterised in that the said polymer contains, expressed as a percentage by weight of each of the constituents, 0.01 to 100%, preferentially 10 to 100%, and very preferentially 20 to 100%, of the organophosphate monomer, and:
a) 0 to 90% at least one other anionic monomer different to the organophosphate monomer,
b) 0 to 50% of at least one non-ionic vinylic monomer,
c) 0 to 20% of at least one non-ionic monomer with a hydrophobic grouping, d) 0 to 10% of at least one organofluorate or organosililate monomer or their blends, e) 0 to 5% of at least one cross-linking monomer, i.e. a monomer having at least 2 polymerisable links, where the said monomer is different from the organophosphate monomers of formulae (Ib), (Id), (If), and (Ih).

where the sum of the percentages by weight of monomers constituting the said polymer is equal to 100.

This process is also characterised in that the anionic monomer a) different from the organophosphate monomer is a monomer with ethylenic unsaturation and with a carboxylic group, chosen from among the monomers with ethylenic unsaturation and with a monocarboxylic group, and is then preferentially acrylic, methacrylic, crotonic, isocrotonic or cinnamic acid, or their blends, or chosen from among the hemiesters of diacids, and is then preferentially a monoester at $C_1$ to $C_4$ of the maleic or itaconic acids, or their blends, or chosen from among the monomers with ethylenic unsaturation and with a dicarboxylic group in the acid or salified state, and preferentially from among itaconic, maleic, fumaric or mesaconic acid, or their blends, or again chosen from among the anhydrides of carboxylic acids, and is then preferentially maleic anhydride.

This process is also characterised in that the vinylic non-ionic monomer b) is chosen from among the esters, amides or nitriles of acrylic and methacrylic acid, and is then very preferentially chosen from among the methyl, ethyl, butyl or 2-ethyl-hexyl acrylates or methacrylates, and their blends, or is chosen from among acrylonitrile, vinyl acetate, styrene, methylstyrene, di-isobutylene, vinylpyrrolidone, vinylcaprolactame and their blends.

This process is also characterised in that the non-ionic monomer with hydrophobic grouping c) is a monomer of formula (II):

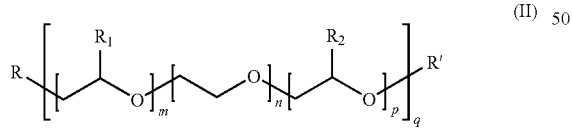

(II)

where:

m and p represent a number of alkylene oxide units of less than or equal to 150, n represents a number of ethylene oxide units of less than or equal to 150, q represents a whole number at least equal to 1 and such that $5 \leq (m+n+p)q \leq 150$, and preferentially such that $15 \leq (m+n+p)q \leq 120$, $R_1$ represents hydrogen or the methyl or ethyl radical, $R_2$ represents hydrogen or the methyl or ethyl radical, R represents a radical containing an unsaturated polymerisable function, preferentially belonging to the group of vinylics, or to the group of acrylic, methacrylic, maleic, itaconic, crotonic or vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or not substituted, or again to the group of ethylenically unsaturated amides or imides, R' represents hydrogen or a hydrocarbonate radical having 5 to 50 atoms of carbon, and represents preferentially a hydrocarbonate radical having 12 to 50 carbon atoms, and very preferentially a hydrocarbonate radical having 16 to 36 carbon atoms, This process is also characterised in that the organofluorate or organosililate monomer d) is a monomer of formula (IIIa) or (IIIb):

with formula (IIIa)

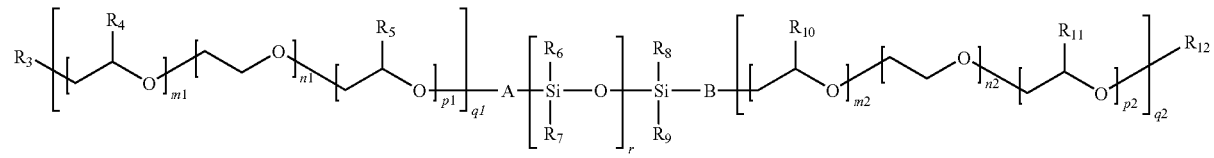

where:

$m_1$, $p_1$, $m_2$ and $p_2$ represent a number of alkylene oxide units of less than or equal to 150, $n_1$ and $n_2$ represent a number of ethylene oxide units of less than or equal to 150, $q_1$ and $q_2$ represent a whole number at least equal to 1 and such that $0 \leq (m_1+n_1+p_1)q_1 \leq 150$ and $0 \leq (m_2+n_2+p_2)q_2 \leq 150$, r represents a number such that $1 \leq r \leq 200$, $R_3$ represents a radical containing an unsaturated polymerisable function, preferentially belonging to the group of vinylics, or to the group of acrylic, methacrylic, maleic, itaconic, crotonic, vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or not substituted, or again to the group of ethylenically unsaturated amides or imides, $R_4$, $R_5$, $R_{10}$ and $R_{11}$ represent hydrogen or the methyl or ethyl radical, $R_6$, $R_7$, $R_8$ and $R_9$ represent linear or branched alkyl or aryl, or alkylaryl or arylalkyl groupings, having 1 to 20 carbon atoms, or their blends, $R_{12}$ represents a hydrocarbon radical having 1 to 40 carbon atoms, A and B are groupings which may be present, which then represent a hydrocarbon radical having 1 to 4 carbon atoms, with formula (IIIb)

$$R\text{-}A\text{-}Si(OB)_3$$

where:

R represents a radical containing an unsaturated polymerisable function, preferentially belonging to the group of vinylics, or to the group of acrylic, methacrylic, maleic, itaconic, crotonic or vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or riot substituted, or again to the group of ethylenically unsaturated amides or imides, A is a grouping which may be present, which then represents a hydrocarbon radical having 1 to 4 carbon atoms, B represents a hydrocarbonate radical having 1 to 4 carbon atoms, or a blend of several of these monomers, This process is also characterised in that the cross-linking monomer e) is chosen from among the group constituted by ethylene glycol dimethacrylate, trimethylolpropanetriacrylate, allyl acrylate, the allyl maleates, methylene-bis-acrylamide, methylene-bis-methacrylamide, tetrallyloxyethane, the triallylcyanurates, the allyl ethers obtained from polyols such as pentaerythritol, sorbitol or sucrose, or chosen from among the molecules of formula (IV):

$R_{13}$ represents a radical containing an unsaturated polymerisable function, preferentially belonging to the group of vinylics, or to the group of acrylic, methacrylic, maleic, itaconic, crotonic, vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or not substituted, or again to the group of ethylenically unsaturated amides or imides, $R_{14}$, $R_{15}$, $R_{20}$ and $R_{21}$ represent hydrogen or the methyl or ethyl radical, $R_{16}$, $R_{17}$, $R_{18}$ and $R_{19}$ represent linear or branched alkyl or aryl, or alkylaryl or arylalkyl groupings, having 1 to 20 carbon atoms, or their blends, D and E are groupings which may be present, which then represent a hydrocarbon radical having 1 to 4 carbon atoms, or from among the blends of these molecules.

This process is also characterised in that the said polymer has a molecular weight of greater than 80,000 g/mole, preferentially greater than 100,000 g/mole, and very preferentially greater than 120,000 g/mole.

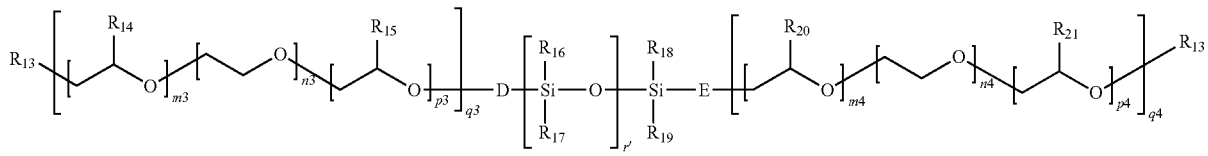

(IV)

where:

$m_3$, $p_3$, $m_4$ and $p_4$ represent a number of alkylene oxide units of less than or equal to 150, $n_3$ and $n_4$ represent a number of ethylene oxide units of less than or equal to 150, $q_3$ and $q_4$ represent a whole number at least equal to 1 and such that $0 \leq (m_3+n_3+p_3)q_3 \leq 150$ and $0 \leq (m_4+n_4+p_4)q_4 \leq 150$, r' represents a number such that $1 \leq r' \leq 200$, Another object of the invention lies in the thickened aqueous compositions, characterised in that they contain as a thickening agent a polymer containing at least one anionic monomer which is an organophosphate monomer, where the said polymer has a molecular weight of greater than 80,000 g/mole, preferentially greater than 100,000 g/mole, and very preferentially greater than 120,000 g/mole.

These aqueous compositions are also characterised in that the organophosphate monomer is chosen from among molecules with the following formulae:

(Ia)
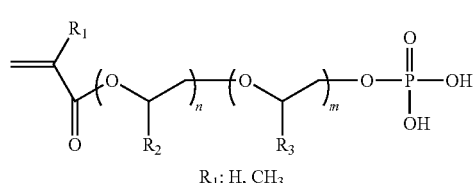
R₁: H, CH₃
R₂: H, CH₃
R₃: H, CH₃
(Ib)
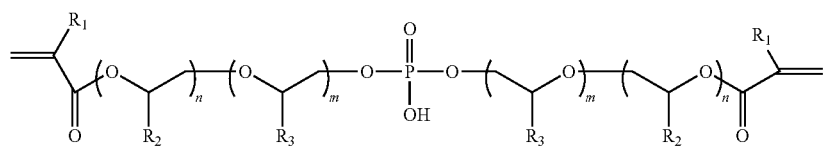
R₁: H, CH₃
R₂: H, CH₃
R₃: H, CH₃
(Ic)
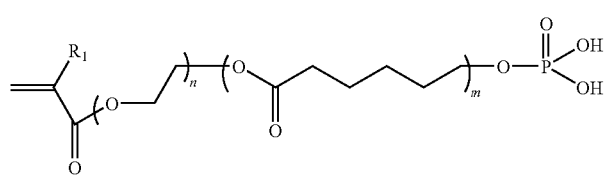
R₁: H, CH₃
(Id)
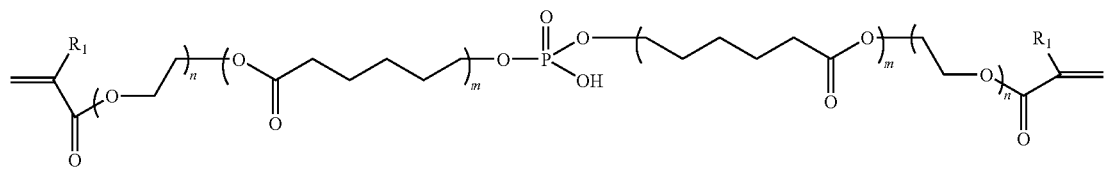
R₁: H, CH₃
(Ie)
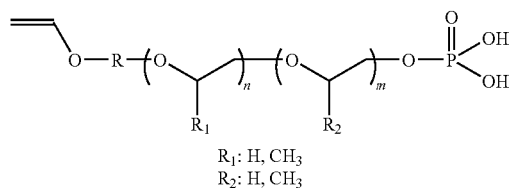
R₁: H, CH₃
R₂: H, CH₃
(If)
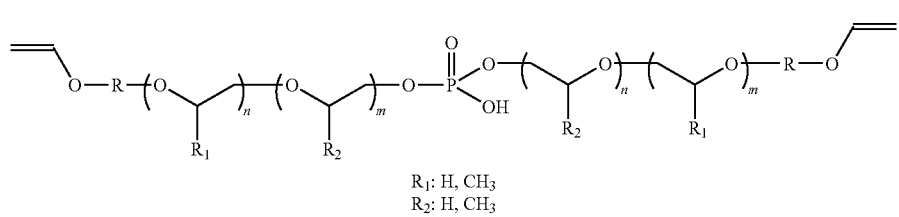
R₁: H, CH₃
R₂: H, CH₃
(Ig)
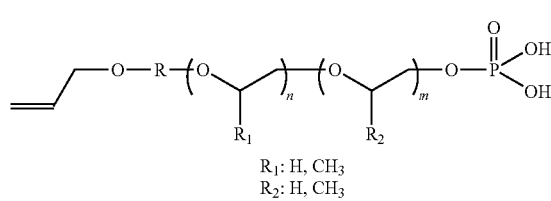
R₁: H, CH₃
R₂: H, CH₃

-continued

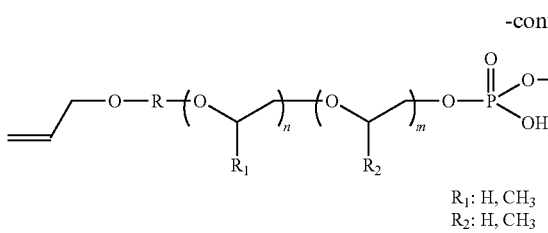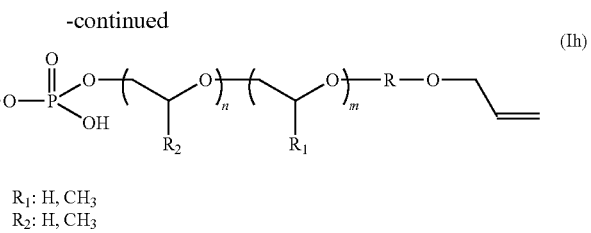

(Ih)

$R_1$: H, CH$_3$
$R_2$: H, CH$_3$ and their blends, where n designates an integer of between 1 and 100, and preferentially between 1 and 20, where m designates an integer of between 0 and 100, and preferentially of between 0 and 20, and R designates an alkyl chain having 2 to 8 carbon atoms.

These aqueous compositions are also characterised in that they have a pH of between 5 and 7, preferentially between 5 and 6.5, and very preferentially between 5.5 and 6.

These aqueous compositions are also characterised in that the said thickening polymer which they contain may contain:
- a) at least one other anionic monomer different to the organophosphate monomer,
- b) and/or at least one vinylic non-ionic monomer,
- c) and/or at least one non-ionic monomer with a hydrophobic grouping,
- d) and/or at least one organofluorate or organosililate monomer or their blends,
- e) and/or at least one cross-linking monomer, i.e. a monomer having at least 2 polymerisable links, where the said monomer is different from the organophosphate monomers of formulae (Ib), (Id), (If), and (Ih), These aqueous compositions are also characterised in that the said thickening polymer which they contain contains, expressed as a percentage by weight of each of the constituents, 0.01 to 100%, preferentially 10 to 100%, and very preferentially 20 to 100% of the organophosphate monomer, and:
- a) 0 to 90% at least one other anionic monomer different to the organophosphate monomer,
- b) 0 to 50% of at least one non-ionic vinylic monomer,
- c) 0 to 20% of at least one non-ionic monomer with a hydrophobic grouping,
- d) 0 to 10% of at least one organofluorate or organosililate monomer or their blends,
- e) 0 to 5% of at least one cross-linking monomer, i.e. a monomer having at least 2 polymerisable links, where the said monomer is different from the organophosphate monomers of formulae (Ib), (Id), (If), and (Ih).

where the sum of the percentages by weight of monomers constituting the said polymer is equal to 100.

These aqueous compositions are also characterised in that the anionic monomer a) of the thickening polymer they contain is a monomer with ethylenic unsaturation and with a carboxylic group, chosen from among the monomers with ethylenic unsaturation and with a monocarboxylic group, and is then preferentially acrylic, methacrylic, crotonic, isocrotonic or cinnamic acid, or their blends, or chosen from among the hemiesters of diacids, and is then preferentially a monoester at $C_1$ to $C_4$ of the maleic or itaconic acids, or their blends, or chosen from among the monomers with ethylenic unsaturation and with a dicarboxylic group in the acid or salified state, and preferentially from among itaconic, maleic, fumaric or mesaconic acid, or their blends, or again chosen from among the anhydrides of carboxylic acids, and is then preferentially maleic anhydride.

These aqueous compositions are also characterised in that the vinylic non-ionic monomer b) of the thickening polymer they contain is chosen from among the esters, amides or nitriles of acrylic and methacrylic acid, and is then very preferentially chosen from among the methyl, ethyl, butyl or 2-ethyl-hexyl acrylates or methacrylates, and their blends, or is chosen from among acrylonitrile, vinyl acetate, styrene, methylstyrene, di-isobutylene, vinylpyrrolidone, vinylcaprolactame and their blends.

These aqueous compositions are also characterised in that the non-ionic monomer with hydrophobic grouping c) of the thickening polymer they contain is a monomer of formula (II):

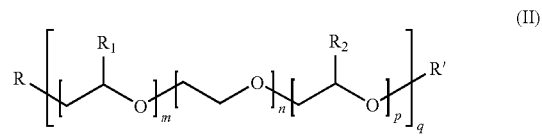

(II)

where:
- m and p represent a number of alkylene oxide units of less than or equal to 150,
- n represents a number of ethylene oxide units of less than or equal to 150,
- q represents a whole number at least equal to 1 and such that $5 \leq (m+n+p)q \leq 150$, and preferentially such that $15 \leq (m+n+p)q \leq 120$,
- $R_1$ represents hydrogen or the methyl or ethyl radical,
- $R_2$ represents hydrogen or the methyl or ethyl radical,
- R represents a radical containing an unsaturated polymerisable function, preferentially belonging to the group of vinylics, or to the group of acrylic, methacrylic, maleic, itaconic, crotonic or vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or not substituted, or again to the group of ethylenically unsaturated amides or imides,
- R' represents hydrogen or a hydrocarbonate radical having 5 to 50 atoms of carbon, and represents preferentially a hydrocarbonate radical having 12 to 50 carbon atoms, and very preferentially a hydrocarbonate radical having 16 to 36 carbon atoms, These aqueous compositions are also characterised in that the organofluorate or organosililate monomer d) of the thickening polymer they contain is a monomer of formula (IIIc) or (IIIb):

with formula (IIIa)

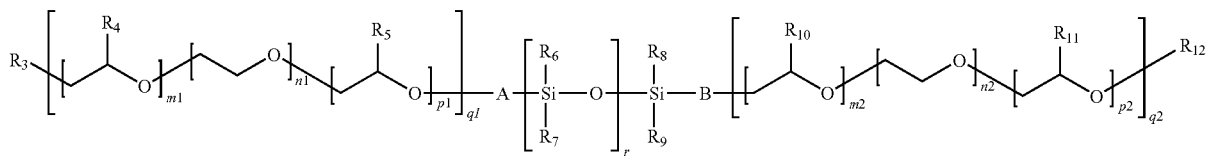

where:
- $m_1$, $p_1$, $m_2$ and $p_2$ represent a number of alkylene oxide units of less than or equal to 150,
- $n_1$ and $n_2$ represent a number of ethylene oxide units of less than or equal to 150,
- $q_1$ and $q_2$ represent a whole number at least equal to 1 and such that $0 \leq (m_1+n_1+p_1)q_1 \leq 150$ and $0 \leq (m_2+n_2+p_2)q_2 \leq 150$,
- r represents a number such that $1 \leq r \leq 200$,
- $R_3$ represents a radical containing an unsaturated polymerisable function, preferentially belonging to the group of vinylics, or to the group of acrylic, methacrylic, maleic, itaconic, crotonic, vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or not substituted, or again to the group of ethylenically unsaturated amides or imides,
- $R_4$, $R_5$, $R_{10}$ and $R_{11}$ represent hydrogen or the methyl or ethyl radical,
- $R_6$, $R_7$, $R_8$ and $R_9$ represent linear or branched alkyl or aryl, or alkylaryl or arylalkyl groupings, having 1 to 20 carbon atoms, or their blends,
- $R_{12}$ represents a hydrocarbon radical having 1 to 40 carbon atoms,
- A and B are groupings which may be present, which then represent a hydrocarbon radical having 1 to 4 carbon atoms, with formula (IIIb)

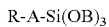

where:
- R represents a radical containing an unsaturated polymerisable function, preferentially belonging to the group of vinylics, or to the group of acrylic, methacrylic, maleic, itaconic, crotonic or vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or not substituted, or again to the group of ethylenically unsaturated amides or imides,
- A is a grouping which may be present, which then represents a hydrocarbon radical having 1 to 4 carbon atoms,
- B represents a hydrocarbonate radical having 1 to 4 carbon atoms, or a blend of several of these monomers, These aqueous compositions are also characterised in that the cross-linking monomer e) of the thickening polymer they contain is chosen from among the group constituted by ethylene glycol dimethacrylate, trimethylolpropanetriacrylate, allyl acrylate, the allyl maleates, methylene-bis-acrylamide, methylene-bis-methacrylamide, tetrallyloxyethane, the triallylcyanurates, the allyl ethers obtained from polyols such as pentaerythritol, sorbitol or sucrose, or chosen from among the molecules of formula (IV):

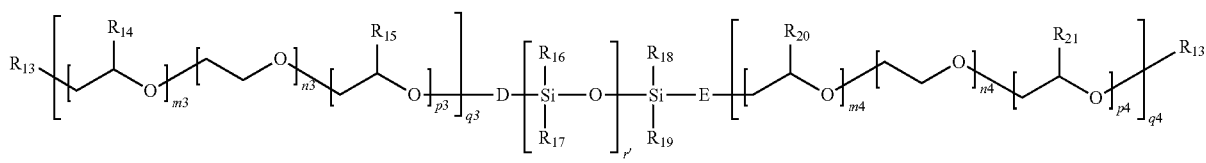

(IV)

where:
- $m_3$, $p_3$, $m_4$ and $p_4$ represent a number of alkylene oxide units of less than or equal to 150,
- $n_3$ and $n_4$ represent a number of ethylene oxide units of less than or equal to 150,
- $q_3$ and $q_4$ represent a whole number at least equal to 1 and such that $0 \leq (m_3+n_3+p_3)q_3 \leq 150$ and $0 \leq (m_4+n_4+p_4)q_4 \leq 150$,
- r' represents a number such that $1 \leq r' \leq 200$,
- $R_{13}$ represents a radical containing an unsaturated polymerisable function, preferentially belonging to the group of vinylics, or to the group of acrylic, methacrylic, maleic, itaconic, crotonic, vinylphthalic esters, or to the group of unsaturated urethanes such as acrylurethane, methacrylurethane, α-α' dimethyl-isopropenyl-benzylurethane, allylurethane, or to the group of allylic or vinylic ethers, whether or not substituted, or again to the group of ethylenically unsaturated amides or imides,
- $R_{14}$, $R_{15}$, $R_{20}$ and $R_{21}$ represent hydrogen or the methyl or ethyl radical,
- $R_{16}$, $R_{17}$, $R_{18}$ and $R_{19}$ represent linear or branched alkyl or aryl, or alkylaryl or arylalkyl groupings, having 1 to 20 carbon atoms, or their blends,
- D and E are groupings which may be present, which then represent a hydrocarbon radical having 1 to 4 carbon atoms, or from among the blends of these molecules.

These aqueous compositions are also characterised in that they are cosmetic or pharmaceutical compositions, compositions with a basis of hydraulic binders, and are then preferentially concretes, cements, mortars, cement slips, slags, detergent compositions, paper coatings or paints.

The following examples illustrate the invention without however limiting its scope.

EXAMPLES

In all the examples the applicant states that the molecular weights of the polymers are determined according to the following method:

It is a method of analysis by Steric Exclusion Chromatography (CES).

The eluent of the CES is tetrahydrofuran.

The flow rate of the product for analysis is 0.8 mL/min.

The product for analysis consists 0.4% by dry weight of the polymer for testing in the mobile phase, also including 0.2% by dry weight of dimethyl formamide.

The CES chain contains an isocratic pump (Waters™ 515), an oven containing a precolumn of the "Guard Column Styragel Waters™" type, two linear columns measuring 7.8 mm internal diameter and 30 cm in length of the "Styragel™ Waters HR4E" type, and a refractometric detector of the RI Waters™ 410 type.

The temperature of the columns and of the detector is set at 35° C.

The detection and processing application of the chromatogram is the PSS win GPC scientific application V 4.02.

The CES is calibrated by a series of 5 sodium poly(acrylate) standards supplied by Polymer Standards Service™.

The column is calibrated by means of polyethylene glycol standards supplied by Polymer Standards Service (PSS), and of molecular weights of between 3,000 and 12,000 g/mole.

Example 1

This example illustrates the process according to the invention, with a view to thickening an aqueous composition which is a cosmetic formulation of night cream, through the introduction into the said composition for thickening of a polymer containing an organophosphate monomer.

This example also illustrates the process according to the invention in which the said polymer is used in the form of an aqueous dispersion.

This example also illustrates the process according to the invention in which the thickening phenomenon occurs at an acid pH of between 5.5 and 5.6.

Finally, this example also illustrates the aqueous composition according to the invention which is a night cream, and which contains the said polymer.

Test n° 1

For test n° 1 illustrating the invention a night cream formulation is produced, the composition of which is given in table 1.

This test illustrates the invention and uses an aqueous dispersion consisting of:

80% by weight of water,

20% by weight of a polymer of molecular weight equal to 135,000 g/mole, where the said polymer consists, expressed as a percentage by weight of the monomers, of:

35% of a blend of monomers of formula (Ia) and of formula (Ib) in which $R_1$=$CH_3$, $R_2$=H, n=1, m=0 a) 30% of methacrylic acid, b) 24.8% of ethyl acrylate, c) 10.2% of a monomer of formula (II), with:
   R designating the methacrylate grouping,
   $R_1$ and $R_2$ designating hydrogen, $n+m+p=25$ R' designating the hydrocarbonate radical having 22 carbon atoms.

TABLE 1

Composition of the cream for 100 g of finished product

| Order of introduction | INCI (International Nomenclature of Cosmetic Ingredients) names of the compounds | Weight (g) |
|---|---|---|
| A | Propylene Glycol Dipelargonate | 6.00 |
| A | Sucrose Distearate | 3.50 |
| A | Isostearyl Isostearate | 6.00 |
| A | Cyclomethicone | 4.00 |
| A | Hydrogenated Polydecene | 4.00 |
| A | Phenoxyethanol (and) Methylparaben (and) Ethylparaben (and) Butylparaben (and) Propylparaben (and) Isobutylparaben | 0.50 |
| A | Sucrose Stearate | 1.50 |
| B | Demineralised water | 71.00 |
| B | Aqueous dispersion containing the organophosphate polymer | 3.30 |
| C | Sodium hydroxide 10% (qsp pH 5.6) | 0.20 |
|   | TOTAL | 100.00 |

The compounds corresponding to the order of introduction [A] are weighed and then melted and homogenised at 70° C.

Under stirring, the compounds corresponding to the order of introduction [B] are then added to the blend, which is then emulsified using a high-speed turbine (6,000 revolutions per minute).

The pH of the emulsion is then raised to a value of 5.5-5.6 using sodium hydroxide [C], whilst the stirring speed is increased to a value of 10,000 revolutions per minute in order to compensate for the increased viscosity.

Test n° 2

This test is a control, for which the same night cream composition was made as that indicated for test n° 1, with the difference that the said composition does not contain the polymer with an organophosphate monomer (the same quantity of demineralised water was introduced in its place).

The compositions corresponding to tests n° 1 and 2 were stored in a flask which was closed for 24 hours at 25° C. After this time the viscosity of the formulation is measured using a Brookfield™ viscometer at speeds of 2.5, 5, 10, 20, 50 and 100 revolutions per minute, and the results are shown in table 2.

TABLE 2

Measurement of the Brookfield ™ viscosity (mPa · s) of the cream

| Measurement speed | Test n° 2 (control) | Test n° 1 (invention) |
|---|---|---|
| 2.5 revolutions per minute | 26000 | 81000 |
| 5 revolutions per minute | 14200 | 44500 |
| 10 revolutions per minute | 8000 | 24250 |
| 20 revolutions per minute | 4500 | 13250 |
| 50 revolutions per minute | 2180 | 6150 |
| 100 revolutions per minute | 1260 | 3650 |

The results of table 2 demonstrate the very marked thickening effect obtained at a pH of between 5.5 and 5.6 in the case of the invention, i.e. through the use of the polymer containing the organophosphate monomer.

Example 2

This example illustrates the process according to the invention, with a view to thickening a composition which is a cosmetic emulsion of body care cream, through the introduction into the said composition for thickening of a polymer containing an organophosphate monomer.

This example also illustrates the process according to the invention in which the said polymer is used in the form of an aqueous dispersion.

This example also illustrates the process according to the invention in which the thickening phenomenon occurs at an acid pH of between 5.5 and 5.6.

Finally, this example also illustrates the aqueous composition according to the invention which is a body care cream cosmetic emulsion, and which contains the said polymer.

For tests n° 3 to 11, a body care cream formulation was produced, the composition of which is given in table 3.

Test n° 3

Test n° 3 illustrates the prior art and uses a polymer consisting of ethyl acrylate, methacrylic acid and ethylene glycol dimethacrylate.

Test n° 4

This test illustrates the invention and uses an aqueous dispersion consisting of:
- 80% by weight of water,
- 20% by weight of a polymer of molecular weight equal to 125,000 g/mole, where the said polymer consists, expressed as a percentage by weight of the monomers, of:
  - 35% of a blend of monomers of formula (Ia) and of formula (Ib) in which $R_1$=$CH_3$, $R_2$=$CH_3$, $R_3$=H, n=6, m=3,
  - a) 30.0% of methacrylic acid,
  - b) 24.8% of ethyl acrylate,
  - c) 10.2% of a monomer of formula (II), with:
    R designating the methacrylate grouping,
    $R_1$ and $R_2$ designating hydrogen, $n+m+p=25$ R' designating the hydrocarbonate radical having 22 carbon atoms.

Test n° 5

This test illustrates the invention and uses an aqueous dispersion consisting of:
- 80% by weight of water,
- 20% by weight of a polymer of molecular weight equal to 124,000 g/mole, where the said polymer consists, expressed as a percentage by weight of the monomers, of:
  - 35% of a blend of formula (Ia) and (Ib) in which $R_1$=$CH_3$, $R_2$=H, $R_3$=H, n+m=100,
  - a) 30.0% of methacrylic acid,
  - b) 24.8% of ethyl acrylate,
  - c) 10.2% of a monomer of formula (II), with:
    R designating the methacrylate grouping,
    $R_1$ and $R_2$ designating hydrogen, $n+m+p=25$ R' designating the hydrocarbonate radical having 22 carbon atoms.

Test n° 6

This test illustrates the invention and uses an aqueous dispersion consisting of:
- 80% by weight of water,
- 20% by weight of a polymer of molecular weight equal to 108,000 g/mole, where the said polymer consists, expressed as a percentage by weight of the monomers, of:
  - 35% of a blend of monomers of formula (Ic) and of formula (Id) in which $R_1$=$CH_3$, n=1, m=2,
  - a) 30.0% of methacrylic acid,
  - b) 24.8% of ethyl acrylate,
  - c) 10.2% of a monomer of formula (II), with:
    R designating the methacrylate grouping,
    $R_1$ and $R_2$ designating hydrogen, $n+m+p=25$ R' designating the hydrocarbonate radical having 22 carbon atoms.

Test n° 7

This test illustrates the invention and uses an aqueous dispersion consisting of:
- 80% by weight of water,
- 20% by weight of a polymer of molecular weight equal to 150,000 g/mole, where the said polymer consists, expressed as a percentage by weight of the monomers, of:
  - 35% of a blend of monomers of formula (Ia) and of formula (Ib) in which $R_1$=$CH_3$, $R_2$=H, n=1, m=0
  - a) 39% of methacrylic acid,
  - b) 20% of ethyl acrylate,
  - c) 6% of a monomer of formula (II), with:
    R designating the methacrylate grouping,
    $R_1$ and $R_2$ designating hydrogen, $n+m+p=25$ R' designating the hydrocarbonate radical having 22 carbon atoms.

Test n° 8

This test illustrates the invention and uses an aqueous dispersion consisting of:
- 80% by weight of water,
- 20% by weight of a polymer of molecular weight equal to 117,000 g/mole, where the said polymer consists, expressed as a percentage by weight of the monomers, of:
  - 35% of a blend of monomers of formula (Ia) and of formula (Ib) in which $R_1$=$CH_3$, $R_2$=H, n=1, m=0
  - a) 20% of methacrylic acid,
  - b) 39% of ethyl acrylate,
  - c) 6% of a monomer of formula (II), with:
    R designating the methacrylate grouping,
    $R_1$ and $R_2$ designating hydrogen, $n+m+p=25$ R' designating the hydrocarbonate radical having 22 carbon atoms.

Test n° 9

This test illustrates the invention and uses an aqueous dispersion consisting of:
- 80% by weight of water,
- 20% by weight of a polymer of molecular weight equal to 145,000 g/mole, where the said polymer consists, expressed as a percentage by weight of the monomers, of:
  - 35% of a blend of monomers of formula (Ia) and of formula (Ib) in which $R_1$=$CH_3$, $R_2$=H, n=1, m=0
  - a) 36% of methacrylic acid,
  - b) 20% of ethyl acrylate,
  - c) 9% of a monomer of formula (II), with:
    R designating the methacrylate grouping,
    $R_1$ and $R_2$ designating hydrogen, $n+m+p=25$ R' designating the hydrocarbonate radical having 22 carbon atoms.

Test n° 10

This test illustrates the invention and uses an aqueous dispersion consisting of:

80% by weight of water,

20% by weight of a polymer of molecular weight equal to 142,500 g/mole, where the said polymer consists, expressed as a percentage by weight of the monomers, of:

35% of a blend of monomers of formula (Ia) and of formula (Ib) in which $R_1$=$CH_3$, $R_2$=H, n=1, m=0 a) 38% of methacrylic acid, b) 20% of ethyl acrylate, c) 7% of a monomer of formula (II), with:

R designating the methacrylate grouping, $R_1$ and $R_2$ designating hydrogen, n+m+p=25

R' designating the hydrocarbonate radical having 22 carbon atoms.

Test n° 11

This test illustrates the invention and uses an aqueous dispersion consisting of:

80% by weight of water,

20% by weight of a polymer of molecular weight equal to 105,500 g/mole, where the said polymer consists, expressed as a percentage by weight of the monomers, of:

35% of a blend of monomers of formula (Ia) and of formula (Ib) in which $R_1$=$CH_3$, $R_2$=H, n=1, m=0 a) 30.7% of methacrylic acid, b) 25.3% of ethyl acrylate, c) 9% of a monomer of formula (II), with:

R designating the methacrylate grouping, $R_1$ and $R_2$ designating hydrogen, n+m+p=25

R' designating the hydrocarbonate radical having 22 carbon atoms.

TABLE 3

Composition of the emulsion for 100 g of finished product

| Order of introduction | INCI names of the compounds | Weight (g) |
|---|---|---|
| A | Cetyl Alcohol (and) Glyceryl Stearate (and) PEG-75 Stearate (and) Ceteth-20 (and) Steareth-20 | 3.00 |
| A | Octyl Dodecyl Myristate | 3.00 |
| A | Caprylic/Capric Triglyceride | 3.00 |
| A | Dimethicone | 4.00 |
| A | Cyclomethicone | 5.00 |
| A | Isopropyl Palmitate | 3.00 |
| A | Phenoxyethanol (and) Methylparaben (and) Ethylparaben (and) Butylparaben (and) Propylparaben (and) Isobutylparaben | 0.50 |
| B | Demineralised water | 69.84 |
| B | Aqueous dispersion containing the thickening polymer | 3.30 |
| C | Sodium hydroxide 10% (qsp pH 5.6) | 0.16 |
| D | Perfume | 0.20 |
| E | Hydrolyzed Soy Protein | 5.00 |
| | TOTAL | 100.00 |

The compounds corresponding to the order of introduction [A] are weighed and then melted and homogenised at 70° C.

Under stirring, the compounds corresponding to the order of introduction [B] are then added to the blend, which is then emulsified using a high-speed turbine (6,000 revolutions per minute).

The pH of the emulsion is then raised to a value of 5.5-5.6 using sodium hydroxide [C], whilst the stirring speed is increased to a value of 10,000 revolutions per minute in order to compensate for the increased viscosity.

Whilst continuing to stir, the remaining ingredients [D] and [E] are added and homogenised.

Test n° 12

This test is a control produced without thickening agent. The quantity of aqueous dispersion containing the thickening agent was replaced in the formulation by the same quantity of demineralised water.

The formulations corresponding to tests n° 3 and 12 were stored in a flask which was closed for 24 hours at 25° C. After this time the viscosity of the formulation is measured using a Brookfield™ viscometer at speeds of 2.5, 5, 10, 20, 50 and 100 revolutions per minute, and the results are shown in table 4.

TABLE 4

Measurement of the Brookfield ™ viscosity (mPa · s) of the cream

| Measurement speed | Test n° 12 (control) | Test n° 3 (prior art) | Test n° 4 (invention) | Test n° 5 (invention) | Test n° 6 (invention) |
|---|---|---|---|---|---|
| 2.5 rev./min. | 12400 | 12400 | 20000 | 19200 | 14400 |
| 5 rev./min. | 8600 | 9200 | 11000 | 12800 | 10000 |
| 10 rev./min. | 4800 | 6400 | 6750 | 7700 | 6900 |
| 20 rev./min. | 3000 | 3800 | 4000 | 4450 | 4150 |
| 50 rev./min. | 1400 | 1880 | 1950 | 2200 | 2160 |
| 100 rev./min. | 800 | 1140 | 1200 | 1310 | 1260 |

| Measurement speed | Test n° 7 (invention) | Test n° 8 (invention) | Test n° 9 (invention) | Test n° 10 (invention) | Test n° 11 (invention) |
|---|---|---|---|---|---|
| 2.5 rev./min. | 62000 | 19000 | 31000 | 41000 | 16000 |
| 5 rev./min. | 37000 | 12000 | 20000 | 24500 | 11500 |
| 10 rev./min. | 21500 | 8500 | 12250 | 15000 | 7500 |
| 20 rev./min. | 12500 | 4875 | 7625 | 8625 | 4625 |
| 50 rev./min. | 5500 | 2600 | 3700 | 4150 | 2350 |
| 100 rev./min. | 3100 | 1550 | 2300 | 2500 | 1425 |

The results of table 4 show that, for a pH of between 5.5 and 5.6, the thickening effect is greater in the case of the invention than in that of the control and of the prior art, whatever the speed of measurement of the Brookfield™ viscosity.

Example 3

This example illustrates the process according to the invention, with a view to thickening a composition which is a cosmetic formulation of body fluid milk, through the introduction into the said composition for thickening of a polymer containing an organophosphate monomer.

This example also illustrates the process according to the invention in which the said polymer is used in the form of an aqueous dispersion.

This example also illustrates the process according to the invention in which the thickening phenomenon occurs at an acid pH of between 6.2 and 6.3.

Finally, this example also illustrates the aqueous composition according to the invention which is a cosmetic formulation of body fluid milk, and which contains the said polymer.

Test n° 13

For test n° 13 illustrating the invention a body fluid milk formulation is produced, the composition of which is given in table 5.

This test illustrates the invention and uses an aqueous dispersion consisting of:
80% by weight of water,
20% by weight of a polymer of molecular weight equal to 124,000 g/mole, where the said polymer consists, expressed as a percentage by weight of the monomers, of:
35% of a blend of formula (Ia) and (Ib) in which $R_1=CH_3$, $R_2=H$, $R_3=H$, n+m=100,
a) 30.0% of methacrylic acid,
b) 24.8% of ethyl acrylate,
c) 10.2% of a monomer of formula (II), with:
R designating the methacrylate grouping,
$R_1$ and $R_2$ designating hydrogen, n+m+p=25

R' designating the hydrocarbonate radical having 22 carbon atoms.

TABLE 5

Composition of the milk for 100 g of finished product

| Order of introduction | INCI names of the compounds | Weight (g) |
|---|---|---|
| A | Propylene Glycol Dipelargonate | 6.00 |
| A | Hydrogenated Polydecene | 5.00 |
| A | Caprylic/Capric Triglyceride | 3.00 |
| A | Tocopheryl Acetate | 0.50 |
| A | Phenoxyethanol (and) Methylparaben (and) Ethylparaben (and) Butylparaben (and) Propylparaben (and) Isobutylparaben | 0.50 |
| B | Propylene Glycol Dipelargonate | 1.00 |
| B | Aqueous dispersion containing the thickening polymer | 3.38 |
| C | Demineralised water | 80.32 |
| D | Sodium hydroxide 10% (qsp pH 5.6) | 0.30 |
| | TOTAL | 100.00 |

The compounds corresponding to the order of introduction [A] are weighed and then homogenised.

The compounds corresponding to the order of introduction [B] are weighed, homogenised and then blended with the compound corresponding to the order of introduction [C].

Whilst stirring, the blend of the compounds corresponding to the orders of introduction [B] and [C] is introduced into the blend corresponding to the order of introduction [A], and the resulting blend is then emulsified by means of a high-speed turbine (6,000 revolutions per minute).

Stirring is maintained at 6,000 revolutions per minute

The pH of the milk is then raised to a value of 6.2-6.3 using sodium hydroxide [D].

Test n° 14

This test is a control, for which the same body fluid milk composition was made as that indicated for test n° 13, with the difference that the said composition does not contain the polymer with an organophosphate monomer (the same quantity of demineralised water was introduced in the place of the aqueous dispersion containing the said polymer).

The compositions corresponding to tests n° 13 and 14 were stored in a flask which was closed for 24 hours at 25° C. After this time the viscosity of the formulation is measured using a Brookfield™ viscometer at speeds of 2.5, 5, 10, 20, 50 and 100 revolutions per minute, and the results are shown in table 6.

TABLE 6

Measurement of the Brookfield ™ viscosity of the body milk

| Measurement speed | Test n° 13 (invention) |
|---|---|
| 2.5 revolutions per minute | 10400 |
| 5 revolutions per minute | 6700 |
| 10 revolutions per minute | 4225 |
| 20 revolutions per minute | 2562 |
| 50 revolutions per minute | 1285 |
| 100 revolutions per minute | 752 |

The control formulation produced according to test n° 14 proved too fluid, and it was impossible to determine the value of the viscosity, whatever the measurement speed.

The results obtained for test n° 13 show the very marked thickening effect obtained through the use of the polymer according to the invention, at a pH of between 6.2 and 6.3, compared to the control formulation.

Example 4

This example illustrates the process according to the invention, with a view to thickening a composition which is a cosmetic formulation of anti-ageing day cream, through the introduction into the said composition for thickening of a polymer containing an organophosphate monomer.

This example also illustrates the process according to the invention in which the said polymer is used in the form of an aqueous dispersion.

This example also illustrates the process according to the invention in which the thickening phenomenon occurs at an acid pH of between 5.5 and 5.6.

Finally, this example also illustrates the aqueous composition according to the invention which is a day cream, and which contains the said polymer.

Test n° 15

For test n° 15 illustrating the invention a day cream formulation is produced, the composition of which is given in table 7.

This test illustrates the invention and uses an aqueous dispersion consisting of:
80% by weight of water,
20% by weight of a polymer of molecular weight equal to 129,000 g/mole, where the said polymer consists, expressed as a percentage by weight of the monomers, of:
- 35% of a blend of formula (Ia) and (Ib) in which $R_1$=$CH_3$, $R_2$=H, $R_3$=H, n+m=100,
  - a) 30.0% of methacrylic acid,
  - b) 24.8% of ethyl acrylate,
  - c) 10.2% of a monomer of formula (II), with:
    R designating the methacrylate grouping,
    $R_1$ and $R_2$ designating hydrogen, $n+m+p=25$ R' designating the hydrocarbonate radical having 22 carbon atoms.

TABLE 7

Composition of the emulsion for 100 g of finished product

| Order of introduction | INCI names of the compounds | Weight (g) |
|---|---|---|
| A | Dimethicone | 4.00 |
| A | Ethylhexylmethoxycinnamate | 5.00 |
| A | Benzophenone-3 | 1.00 |
| A | Ethoxydiglycol Oleate | 6.00 |
| A | Tocopheryl Acetate | 0.50 |
| A | Cetyl Alcohol | 2.50 |
| A | Stearyl Alcohol | 2.50 |
| A | Propylene Glycol Laurate (and) Ethylcellulose (and) Propylene Glycol Isostearate | 6.00 |
| B | Demineralised water | 56.40 |
| B | Aqueous dispersion containing the thickening polymer | 2.45 |
| C | Aluminum Starch Octenylsuccinate | 4.00 |
| C | Glycerin | 2.00 |
| C | Butylene Glycol | 2.00 |
| C | Dimethicone (and) Dimethiconol | 2.00 |
| D | Perfume | 0.15 |
| D | Yellow 6 | 0.40 |
| D | Water (and) Fagus Sylvatica Bud Extract | 3.00 |
| E | Aminomethyl Propanol (qsp pH 5.5-5.6) | 0.10 |
|   | TOTAL | 100.00 |

The compounds corresponding to the order of introduction [A] are weighed and then melted and homogenised at 70° C.

Under stirring, the compounds corresponding to the order of introduction [B] are then added to the blend, which is then emulsified using a high-speed turbine (6,000 revolutions per minute).

The temperature of the blend is then reduced to 50° C., and the compounds corresponding to the order of introduction [C] are then added whilst stirring is maintained.

Whilst stirring is maintained, the compounds corresponding to the order of introduction [D] are then added, and the pH is then adjusted to a value of between 5.5 and 5.6 using the compound corresponding to the order of introduction [E].

Test n° 16

This test is a control, for which the same day cream composition was made as that indicated for test n° 15, with the difference that the said composition does not contain the polymer with an organophosphate monomer (the same quantity of demineralised water was introduced in the place of the aqueous dispersion containing the thickening polymer).

The finished formulation is stored in a flask closed for 24 hours at 25° C. After this time the viscosity of the formulation is measured using a Brookfield™ viscometer at speeds of 2.5, 5, 10, 20, 50 and 100 revolutions per minute, and the results are shown in table 8.

TABLE 8

Measurement of the Brookfield ™ viscosity of the day cream

| Measurement speed | Test n° 16 (control) | Test n° 15 (invention) |
|---|---|---|
| 2.5 revolutions per minute | 23000 | 32000 |
| 5 revolutions per minute | 17500 | 20000 |
| 10 revolutions per minute | 9750 | 12750 |
| 20 revolutions per minute | 5750 | 7500 |
| 50 revolutions per minute | 3000 | 4200 |
| 100 revolutions per minute | 1600 | 2600 |

The results of table 8 demonstrate the very marked thickening effect obtained at a pH of between 5.5 and 5.6 in the case of the invention, i.e. through the use of the polymer containing the organophosphate monomer.

Example 5

This example illustrates the process according to the invention, with a view to thickening a gel in water, through the introduction of a polymer containing an organophosphate monomer.

This example also illustrates the process according to the invention in which the said polymer is used in the form of an aqueous dispersion.

This example notably illustrates the capacity of the polymers according to the invention to develop a thickening effect at lower pHs than the pHs for which the polymers of the prior art develop this effect.

For each of the tests n° 17 to 20, an aqueous formulation having a final thickening polymer content of 3% by dry weight of polymer relative to the total weight of the formulation is prepared, proceeding as indicated below.

In a 600 ml beaker, 15 g by dry weight of the thickening polymer for testing and 500 g qsp of deionised water are weighed.

The blend obtained is then subjected to moderate stirring in order to produce a satisfactory blend, without however incorporating air into the medium.

Test n° 17

This test illustrates the prior art and uses a polymer which is an acrylic copolymer sold by the company NOVEON™ under the name Carbopol™ Aqua SF1.

Test n° 18

This test illustrates the prior art and uses a polymer which is a terpolymer of methacrylic acid, ethyl acrylate and ethylene glycol dimethacrylate.

Test n° 19

This test illustrates the invention and uses an aqueous dispersion consisting of:
- 80% by weight of water,
- 20% by weight of a polymer of molecular weight equal to 132,000 g/mole, where the said polymer consists, expressed as a percentage by weight of the monomers, of:
  - 35% of a blend of monomers of formula (Ia) and of formula (Ib) in which $R_1$=$CH_3$, $R_2$=H, n=1, m=0
    - a) 30.0% of methacrylic acid,
    - b) 24.8% of ethyl acrylate,
    - c) 10.2% of a monomer of formula (II), with:
      R designating the methacrylate grouping,
      $R_1$ and $R_2$ designating hydrogen, $n+m+p=25$ R' designating the hydrocarbonate radical having 22 carbon atoms.

Test n° 20

This test illustrates the invention and uses an aqueous dispersion consisting of:
- 80% by weight of water,
- 20% by weight of a polymer of molecular weight equal to 131,500 g/mole, where the said polymer consists, expressed as a percentage by weight of the monomers, of:
  - 35% of a blend of monomers of formula (Ia) and of formula (Ib) in which $R_1$=$CH_3$, $R_2$=H, n=1, m=0
    a) 28.9% of methacrylic acid,
    b) 23.6% of ethyl acrylate,
  - c) 12.5% of a monomer of formula (II), with:
    R designating the methacrylate grouping,
    $R_1$ and $R_2$ designating hydrogen, $n+m+p=25$ R' designating the hydrocarbonate radical having 22 carbon atoms.

The pH of the formulation is checked continuously using a pH meter.

Small quantities of sodium hydroxide (10%) are then added, and the formulation is then blended until the pH is stabilised, and the Brookfield™ viscosity is measured at 100 revolutions per minute (see table 9).

This operation is repeated until the viscosity increases rapidly, with the line of the graph becoming almost vertical. The rise of viscosity enables the pH from which the polymer viscosifies the medium to be determined clearly.

The viscosity measurements are shown in table 9.

This example also illustrates the process according to the invention in the variant according to which the back-acid technique is used.

The following procedure enables the capacity of a polymer of the invention to develop its thickening power at a satisfactory pH level using the back-acid technique to be quantified. According to this method the pH of the formulation containing the polymer is raised to a value of approximately 8 and then brought back down to a pH of 4. This technique enables the polymer's useful pH to be highlighted.

Test n° 21

To accomplish this an aqueous formulation is prepared, proceeding as follows:

In a 600 ml beaker, 25 g of an aqueous dispersion of the polymer for testing and 500 qsp of deionised water are weighed, where the polymer for testing is a polymer according to the invention.

The said aqueous dispersion consists of:
- 80% by weight of water,
- 20% by weight of a polymer of molecular weight equal to 128,000 g/mole, where the said polymer consists, expressed as a percentage by weight of the monomers, of:
  - 35% of a blend of monomers of formula (Ia) and of formula (Ib) in which $R_1$=$CH_3$, $R_2$=H, n=1, m=0
    a) 30.0% of methacrylic acid,
    b) 24.8% of ethyl acrylate,
  - c) 10.2% of a monomer of formula (II), with:

TABLE 9

| | Test n° 17<br>Prior art | | Test n° 18<br>Prior art | | Test n° 19<br>Polymer of the invention | | Test n° 20<br>Polymer of the invention |
|---|---|---|---|---|---|---|---|
| pH | Brookfield™<br>viscosity at 100<br>revolutions per minute<br>(mPa·s) | pH | Brookfield™<br>viscosity at 100<br>revolutions per minute<br>(mPa·s) | pH | Brookfield™<br>viscosity at 100<br>revolutions per minute<br>(mPa·s) | pH | Brookfield™<br>viscosity at 100<br>revolutions per minute<br>(mPa·s) |
| 5.00 | 20.00 | 5.54 | 12.00 | 5.00 | 30.00 | 5.00 | 32.00 |
| 6.10 | 20.00 | 5.95 | 26.00 | 5.20 | 40.00 | 5.20 | 40.00 |
| 6.25 | 64.00 | 6.12 | 70.00 | 5.35 | 74.00 | 5.30 | 50.00 |
| 6.35 | 176.00 | 6.15 | 220.00 | 5.50 | 480.00 | 5.40 | 80.00 |
| 6.40 | 725.00 | 6.18 | 690.00 | 5.60 | 610.00 | 5.45 | 260.00 |
| — | — | 6.20 | 1100.00 | 5.65 | 1360.00 | 5.56 | 1800.00 |

Table 9 enables the change of viscosity as a function of the pH to be represented, for each of the tests n° 17 to 20: FIG. 1/3 represents the change of the Brookfield™ viscosity measured at 100 revolutions per minute as a function of the pH.

It can be clearly seen by this means that the thickening effect occurs for polymers according to the invention at pHs well below those for which the thickening effect of the polymers according to the prior art occurs.

Example 6

This example illustrates the process according to the invention, with a view to thickening a gel in water, through the introduction of a polymer containing an organophosphate monomer.

This example also illustrates the process according to the invention in which the said polymer is used in the form of an aqueous dispersion.

This example notably illustrates the capacity of the polymers according to the invention to develop a thickening effect at lower pHs than the pHs for which the polymers of the prior art develop this effect.

R designating the methacrylate grouping,
$R_1$ and $R_2$ designating hydrogen, $n+m+p=25$ R' designating the hydrocarbonate radical having 22 carbon atoms.

The blend obtained is then subjected to moderate stirring in order to produce a satisfactory blend, without however incorporating air into the medium.

The pH of the formulation is checked continuously using a pH meter.

Small quantities of sodium hydroxide (10%) are then added, and the formulation is then blended until the pH is stabilised, and the Brookfield™ viscosity of the formulation is measured at 100 revolutions per minute. This operation is repeated until the pH reaches a value of approximately 8. When this value has been reached the pH is brought back down to a value of approximately 4 using lactic acid, added in small quantities, and the pH and the Brookfield™ viscosity at 100 revolutions per minute are measured after each addition of acid.

TABLE 10

| pH of the solution | Brookfield ™ viscosity 100 revolutions per minute (mPa · s) |
|---|---|
| 4.78 | 17 |
| 5.54 | 26 |
| 5.85 | 39 |
| 6 | 61 |
| 6.15 | 106 |
| 6.26 | 200 |
| 6.45 | 380 |
| 6.62 | 458 |
| 7.1 | 550 |
| 8.3 | 624 |
| 8.3 | 624 |
| 7.53 | 500 |
| 6.71 | 240 |
| 6.55 | 187 |
| 6.32 | 145 |
| 6.01 | 117 |
| 5.5 | 68 |
| 5.5 | 68 |
| 4.98 | 50 |

The results are shown in table 10.

Figure 2:
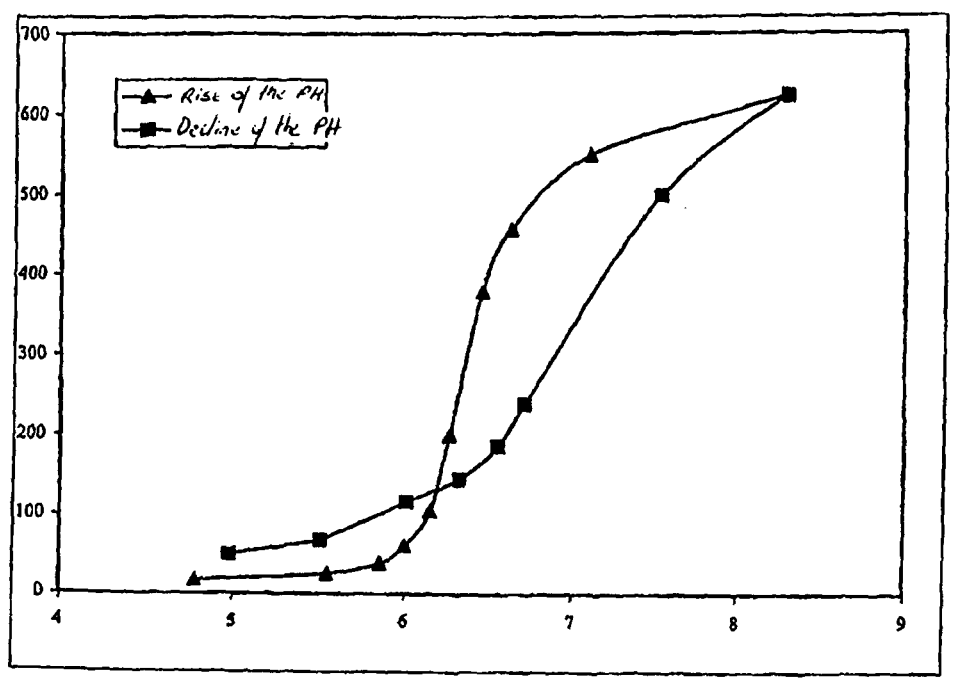

They enable FIG. 2/3 to be established, which represents the change as a function of the pH of the Brookfield viscosity measured at 100 revolutions per minute, during the period in which the pH increases, and during the period in which the pH is reduced.

This illustrates the thickening effect developed by the polymer according to the invention, when it is used in the context of the technique known as the back-acid technique.

Example 7

This example illustrates the process according to the invention, with a view to thickening a gel in water, through the introduction of a polymer containing an organophosphate monomer.

This example also illustrates the process according to the invention in which the said polymer is used in the form of an aqueous dispersion.

This example notably illustrates the capacity of the polymers according to the invention to develop a thickening effect at lower pHs than the pHs for which the polymers of the prior art develop this effect.

For each of the tests n° 22 to 25, an aqueous formulation having a final thickening polymer content of 3% by dry weight of polymer relative to the total weight of the formulation is prepared, proceeding as indicated below.

In a 600 ml beaker, 15 g by dry weight of the thickening polymer for testing and 500 g qsp of deionised water are weighed.

The blend obtained is then subjected to moderate stirring in order to produce a satisfactory blend, without however incorporating air into the medium.

Test n° 22

This test illustrates the prior art and uses a polymer which is an acrylic copolymer sold by the company NOVEON™ under the name Carbopol™ Aqua SF1.

Test n° 23

This test illustrates the invention and uses an aqueous dispersion consisting of:
80% by weight of water,
20% by weight of a polymer of molecular weight equal to 125,000 g/mole, where the said polymer consists, expressed as a percentage by weight of the monomers, of:
35% of a blend of monomers of formula (Ia) and of formula (Ib) in which $R_1$=$CH_3$, $R_2$=H, n=1, m=0
a) 32.4% of methacrylic acid and 3.6% of acrylic acid,
b) 23.0% of ethyl acrylate,
c) 6.0% of a monomer of formula (II), with:
R designating the methacrylate grouping,
$R_1$ and $R_2$ designating hydrogen, $n+m+p=25$ R' designating the hydrocarbonate radical having 22 carbon atoms.

Test n° 24

This test illustrates the invention and uses an aqueous dispersion consisting of:
80% by weight of water,
20% by weight of a polymer of molecular weight equal to 140,500 g/mole, where the said polymer consists, expressed as a percentage by weight of the monomers, of:
35% of a blend of monomers of formula (Ia) and of formula (Ib) in which $R_1$=$CH_3$, $R_2$=H, n=1, m=0
a) 36.0% of methacrylic acid,
b) 23.0% of ethyl acrylate,
c) 6.0% of a monomer of formula (II), with:
R designating the methacrylate grouping,
$R_1$ and $R_2$ designating hydrogen, $n+m+p=25$ R' designating a branched hydrocarbonate radical having 16 carbon atoms.

Test n° 25

This test illustrates the invention and uses an aqueous dispersion consisting of:
80% by weight of water,
20% by weight of a polymer of molecular weight equal to 137,500 g/mole, where the said polymer consists, expressed as a percentage by weight of the monomers, of:
35% of a blend of monomers of formula (Ia) and of formula (Ib) in which $R_1$=$CH_3$, $R_2$=H, n=1, m=0
a) 34.0% of methacrylic acid and 2.0% of ethylene glycol dimethacrylate,
b) 23.0% of ethyl acrylate,
c) 6.0% of a monomer of formula (II), with:
R designating the methacrylate grouping,
$R_1$ and $R_2$ designating hydrogen, $n+m+p=25$ R' designating the hydrocarbonate radical having 22 carbon atoms.

Figure 3:
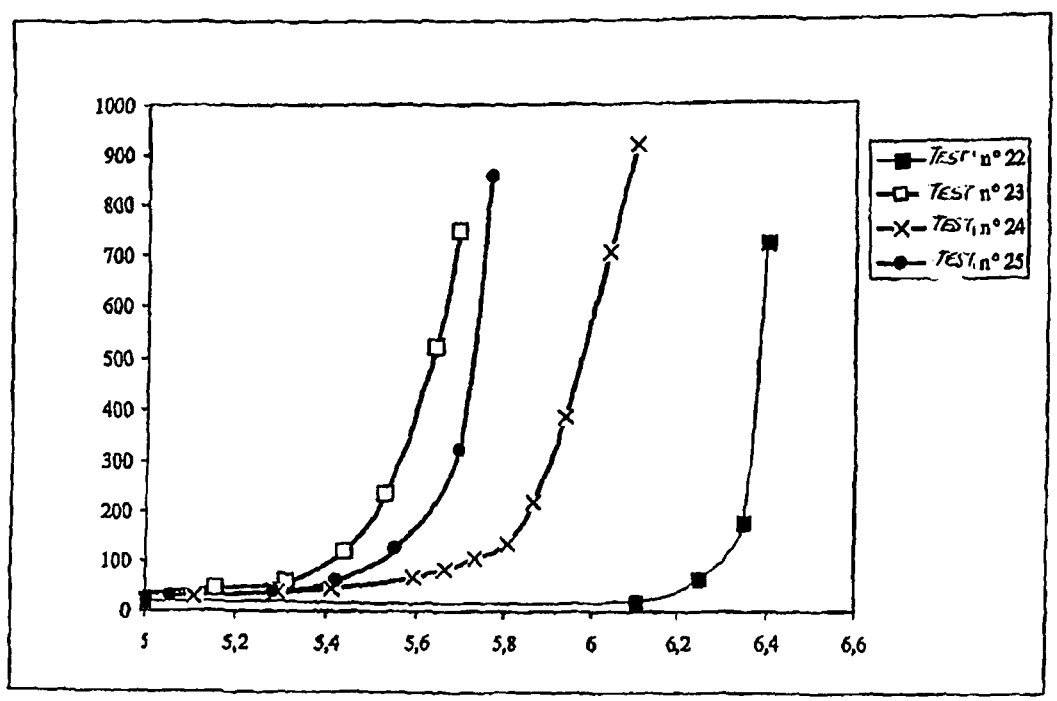

FIG. 3/3 represents the change of the Brookfield™ viscosity measured at 100 revolutions per minute as a function of the pH.

It can be clearly seen by this means that the thickening effect occurs for polymers according to the invention at pHs well below those for which the thickening effect of the polymers according to the prior art occurs.

The invention claimed is:

1. A process for thickening an aqueous composition comprising contacting said aqueous composition with a thickening agent; wherein said aqueous composition is at a pH of between 5 and 7 and said thickening agent comprises at least one polymer containing at least one anionic organophosphate monomer, wherein the at least one anionic monomer is an organophosphate monomer of formula:

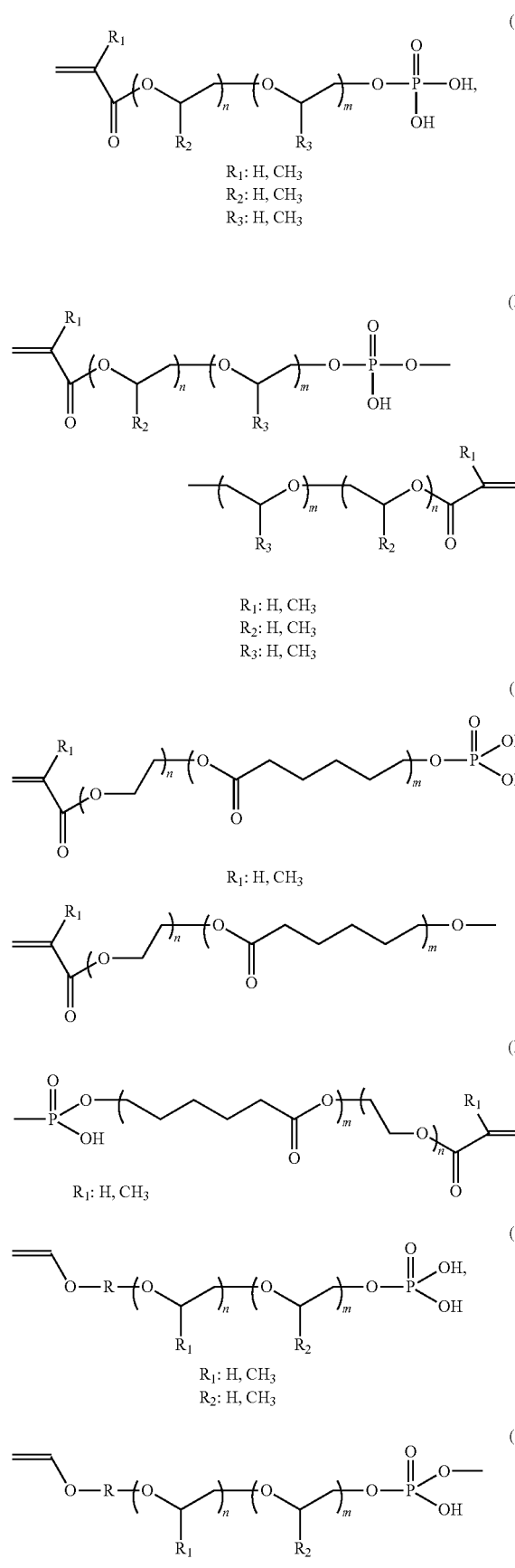
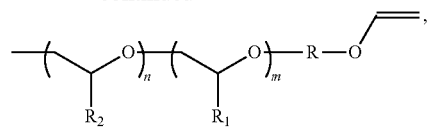
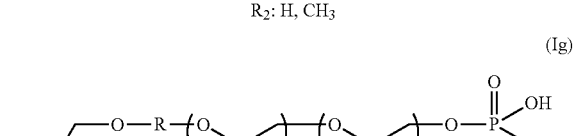
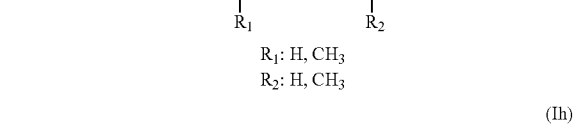
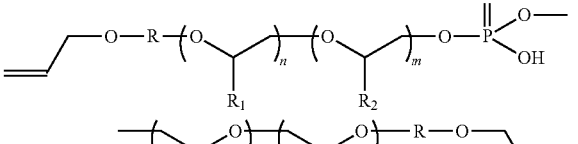
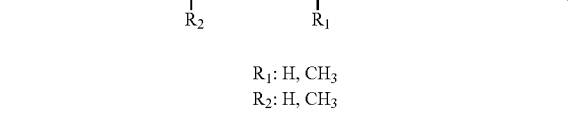

or their blends, where n designates an integer of between 1 and 100, where m designates an integer of between 0 and 100, and R designates an alkyl chain having 2 to 8 carbon atoms.

2. The process according to claim 1, wherein n designates an integer of between 1 and 20, and m designates an integer of between 0 and 20.

3. The process according to claim 1, wherein the composition is contacted with the at least one polymer at a pH of between 5 and 6.5.

4. The process according to claim 1, wherein the composition is contacted with the at least one polymer at a pH of between 5 and 6.

5. The process according to claim 1, wherein the polymer is introduced into the aqueous composition in powder form, in the form of an aqueous dispersion, in the form of a solvent-based dispersion, in the form of a reverse dispersion, in the form of an aqueous solution, or in the form of a solvent-based solution.

6. The process according to claim 1, wherein the pH value is increased by the addition of an alkaline compound and then reduced by the addition of an acid compound using a back-acid technique.

7. The process according to claim 1, wherein the polymer further comprises:
   a) at least one anionic monomer that is not an organophosphate monomer,
   b) and/or at least one vinylic non-ionic monomer,
   c) and/or at least one non-ionic monomer with a hydrophobic grouping,
   d) and/or at least one organofluorate or organosililate monomer or their blends,
   e) and/or at least one cross-linking monomer having at least two polymerizable links.

8. The process according to claim 7, wherein the polymer contains, expressed as a percentage by weight of each of the constituents, 0.01 to 100% of the organophosphate monomer, and:
- a) 0 to 90% of at least one anionic monomer that is not an organophosphate monomer,
- b) 0 to 50% of at least one non-ionic vinylic monomer,
- c) 0 to 20% of at least one non-ionic monomer with a hydrophobic grouping,
- d) 0 to 10% of at least one organofluorate or organosililate monomer or their blends,
- e) 0 to 5% of at least one cross-linking monomer having at least 2 polymerizable links, where the sum of the percentages by weight of monomers constituting the polymer is equal to 100.

9. The process according to claim 8, wherein the polymer contains, expressed as a percentage by weight of each of the constituents, 10 to 100% of the organophosphate monomer.

10. The process according to claim 8, wherein the polymer contains, expressed as a percentage by weight of each of the constituents, 20 to 100% of the organophosphate monomer.

11. The process according to claim 7, wherein the anionic monomer a) is:
- a monomer with ethylenic unsaturation and with a carboxylic group;
- a monomer with ethylenic unsaturation and with a monocarboxylic group, acrylic, methacrylic, crotonic, isocrotonic or cinnamic acid, or their blends, or a hemiesters of a diacids, a monoester at $C_1$ to $C_4$ of maleic or itaconic acids, or their blends;
- a monomer with ethylenic unsaturation and with a dicarboxylic group in the acid or salified state, itaconic, maleic, fumaric or mesaconic acid, or their blends;
- an anhydrides of carboxylic acids;
- or maleic anhydride.

12. The process according to claim 7, wherein the vinylic non-ionic monomer b) is:
- an ester, amide or nitrile of acrylic or methacrylic acid;
- a methyl, ethyl, butyl or 2-ethyl-hexyl acrylates or methacrylates, and their blends;
- an acrylonitrile, vinyl acetate, styrene, methylstyrene, diisobutylene, vinylpyrrolidone, vinylcaprolactame; or their blends.

13. The process according to claim 7, wherein the non-ionic monomer with hydrophobic grouping c) is a monomer of formula (II):

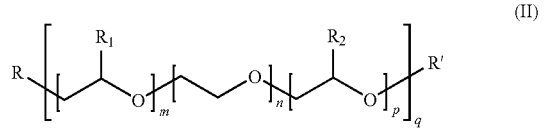

(II)

where:
- m and p represent a number of alkylene oxide units of less than or equal to 150,
- n represents a number of ethylene oxide units of less than or equal to 150,
- q represents a whole number at least equal to 1 and such that $5 \leq (m+n+p)q \leq 150$,
- $R_1$ represents hydrogen or the methyl or ethyl radical,
- $R_2$ represents hydrogen or the methyl or ethyl radical,
- R represents a radical containing an unsaturated polymerisable function, a vinylic, an acrylic, methacrylic, maleic, itaconic, crotonic or vinylphthalic ester, or an unsaturated urethane, acrylurethane, methacrylurethane, α-α' dimethyl-isopropenyl-benzylurethane, allylurethane, or an allylic or vinylic ether, whether or not substituted, or an ethylenically unsaturated amide or imide,
- R' represents hydrogen or a hydrocarbonate radical having 5 to 50 atoms of carbon.

14. The process according to claim 13, wherein q represents a whole number at least equal to 1 and such that $15 \leq (m+n+p)q \leq 120$.

15. The process according to claim 13, wherein R' represents a hydrocarbonate radical having 12 to 50 carbon atoms.

16. The process according to claim 13, wherein R' represents a hydrocarbonate radical having 16 to 36 carbon atoms.

17. A process according to claim 7, wherein the organofluorate or organosililate monomer d) is a monomer of formula (IIIa) or (IIIb):

with formula (IIIa)

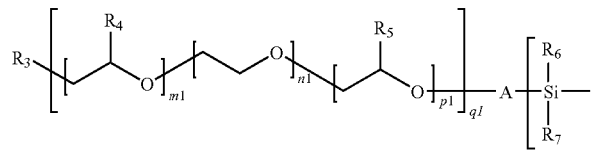

where:
- $m_1$, $p_1$, $m_2$ and $p_2$ represent a number of alkylene oxide units of less than or equal to 150,
- $n_1$ and $n_2$ represent a number of ethylene oxide units of less than or equal to 150,
- $q_1$ and $q_2$ represent a whole number at least equal to 1 and such that $0 \leq (m_1+n_1+p_1)q_1 \leq 150$ and $0 \leq (m_2+n_2+p_2)q_2 \leq 150$,
- r represents a number such that $1 \leq r \leq 200$,
- $R_3$ represents a radical containing an unsaturated polymerisable function, a vinylic, or an acrylic, methacrylic, maleic, itaconic, crotonic, or vinylphthalic ester, or an unsaturated urethane, acrylurethane, methacrylurethane, α-α' dimethyl-isopropenyl-benzylurethane, allylurethane, or an allylic or vinylic ether, whether or not substituted, or an ethylenically unsaturated amide or imide,
- $R_4$, $R_5$, $R_{10}$ and $R_{11}$ represent hydrogen or the methyl or ethyl radical,
- $R_6$, $R_7$, $R_8$ and $R_9$ represent linear or branched alkyl or aryl, or alkylaryl or arylalkyl groupings, having 1 to 20 carbon atoms, or their blends,
- $R_{12}$ represents a hydrocarbon radical having 1 to 40 carbon atoms,
- A and B are groupings which may be present, which then represent a hydrocarbon radical having 1 to 4 carbon atoms, with formula (IIIb)

R-A-Si(OB)$_3$ where:
- R represents a radical containing an unsaturated polymerizable function, a vinylic, or to an acrylic, methacrylic, maleic, itaconic, crotonic or vinylphthalic ester, or an unsaturated urethane, acrylurethane, methacrylurethane, α-α' dimethyl-isopropenyl-benzylurethane, allylurethane, or an allylic or vinylic ether, whether or not substituted, or an ethylenically unsaturated amide or imide,
- A is a grouping which may be present, which then represents a hydrocarbon radical having 1 to 4 carbon atoms,
- B represents a hydrocarbonate radical having 1 to 4 carbon atoms, or a blend of several of these monomers.

18. The process according to claim 7, wherein the cross-linking monomer e) is ethylene glycol dimethacrylate, trimethylolpropanetriacrylate, allyl acrylate, an allyl maleate, methylene-bis-acrylamide, methylene-bis-methacrylamide, tetrallyloxyethane, an triallylcyanurate, an allyl ether obtained from a polyol or entaerythritol, sorbitol or sucrose, or a molecule of formula (IV):

where:
- $m_3$, $p_3$, $m_4$ and $p_4$ represent a number of alkylene oxide units of less than or equal to 150,
- $n_3$ and $n_4$ represent a number of ethylene oxide units of less than or equal to 150,
- $q_3$ and $q_4$ represent a whole number at least equal to 1 and such that $0 \leq (m_3+n_3+p_3)q_3 \leq 150$ and $0 \leq (m_4+n_4+p_4)q_4 \leq 150$,
- r' represents a number such that $1 \leq r' \leq 200$,
- $R_{13}$ represents a radical containing an unsaturated polymerizable function, a vinylic, or an acrylic, methacrylic, maleic, itaconic, crotonic, vinylphthalic ester, or an unsaturated urethane, acrylurethane, methacrylurethane, α-α' dimethyl-isopropenyl-benzylurethane, allylurethane, or an allylic or vinylic ether, whether or not substituted, or an ethylenically unsaturated amide or imide,
- $R_{14}$, $R_{15}$, $R_{20}$ and $R_{21}$ represent hydrogen or the methyl or ethyl radical,
- $R_{16}$, $R_{17}$, $R_{18}$ and $R_{19}$ represent linear or branched alkyl or aryl, or alkylaryl or arylalkyl groupings, having 1 to 20 carbon atoms, or their blends,
- D and E are groupings which may be present, which then represent a hydrocarbon radical having 1 to 4 carbon atoms, or from among the blends of these molecules.

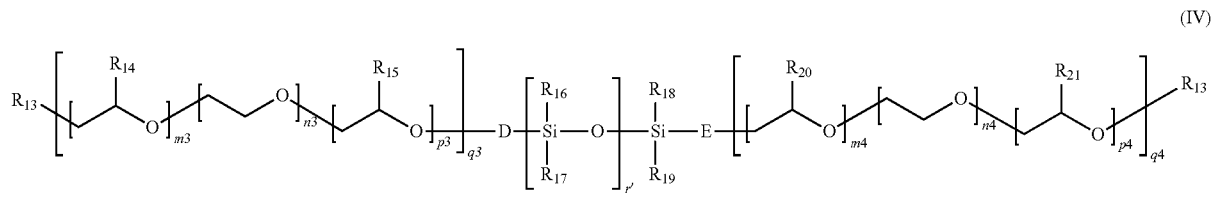

(IV)

19. The process according to claim 1, wherein the polymer has a molecular weight of greater than 80,000 g/mole.

20. The process according to claim 1, wherein the polymer has a molecular weight greater than 100,000 g/mole.

21. The process according to claim 1, wherein the polymer has a molecular weight greater than 120,000 g/mole.

* * * * *